United States Patent
Bärwinkel et al.

(10) Patent No.: US 10,285,674 B2
(45) Date of Patent: May 14, 2019

(54) INSTRUMENT FOR A MANIPULATOR ARM OF AN ENDOSCOPIC ROBOT

(75) Inventors: Ronny Bärwinkel, Dormitz (DE);
Oliver Hornung, Fürth (DE);
Karl-Heinz Maier, Altdorf b. Nürnberg (DE)

(73) Assignee: Siemens Healthcare GmbH, Erlangen (DE)

( * ) Notice: Subject to any disclaimer, the term of this patent is extended or adjusted under 35 U.S.C. 154(b) by 1027 days.

(21) Appl. No.: 13/819,357

(22) PCT Filed: Aug. 29, 2011

(86) PCT No.: PCT/EP2011/064781
§ 371 (c)(1),
(2), (4) Date: May 8, 2013

(87) PCT Pub. No.: WO2012/031920
PCT Pub. Date: Mar. 15, 2012

(65) Prior Publication Data
US 2013/0231682 A1  Sep. 5, 2013

(30) Foreign Application Priority Data
Sep. 8, 2010 (DE) .................. 10 2010 040 415

(51) Int. Cl.
| A61B 17/00 | (2006.01) |
| A61B 1/00 | (2006.01) |
| A61B 17/29 | (2006.01) |
| A61B 34/30 | (2016.01) |
| A61B 90/80 | (2016.01) |
| A61B 46/10 | (2016.01) |

(52) U.S. Cl.
CPC .... *A61B 17/00234* (2013.01); *A61B 1/00135* (2013.01); *A61B 17/29* (2013.01); *A61B 34/30* (2016.02); *A61B 46/10* (2016.02); *A61B 90/80* (2016.02); *A61B 2017/2908* (2013.01)

(58) Field of Classification Search
CPC ..... A61B 19/22; A61B 2019/22; A61B 34/30; A61B 34/70
See application file for complete search history.

(56) References Cited

U.S. PATENT DOCUMENTS

| 5,334,207 A * | 8/1994 | Gay, Jr. ........... A61B 18/245 604/95.01 |
| 5,989,183 A * | 11/1999 | Reisdorf ........... A61B 1/00091 600/121 |
| 7,328,071 B1 * | 2/2008 | Stehr ................ A61N 1/0587 600/585 |

(Continued)

FOREIGN PATENT DOCUMENTS

| DE | 2835331 A1 | 2/1980 |
| WO | WO 2009092701 A1 | 7/2009 |

*Primary Examiner* — Lynsey C Eiseman
(74) *Attorney, Agent, or Firm* — Laurence Greenberg; Werner Stemer; Ralph Locher

(57) ABSTRACT

An instrument for a manipulator arm of an endoscopic robot is provided. The instrument has a treatment head for carrying out a medical measure in a patient, an instrument base carrying the treatment head, a coupling element that can be fastened to the manipulator arm, and a sterilizable sleeve enclosing the instrument and having at least one opening which can be sealingly placed on the instrument base. The coupling element protrudes from the opening.

7 Claims, 3 Drawing Sheets

(56) References Cited

U.S. PATENT DOCUMENTS

| | | |
|---|---|---|
| 2002/0043266 A1 | 4/2002 | Kotin |
| 2005/0143625 A1 | 6/2005 | Brauner |
| 2005/0255424 A1* | 11/2005 | Hack ............... A61B 5/0088 433/29 |
| 2006/0025652 A1* | 2/2006 | Vargas ............ A61B 1/00154 600/114 |
| 2006/0079884 A1 | 4/2006 | Krom |
| 2006/0079889 A1* | 4/2006 | Scott ............... A61B 17/3201 606/45 |
| 2007/0129634 A1 | 6/2007 | Hickey |
| 2008/0078388 A1* | 4/2008 | Vandine ............ A61M 16/04 128/204.21 |
| 2009/0248039 A1 | 10/2009 | Cooper |
| 2011/0004157 A1* | 1/2011 | Dewaele ........... A61B 1/00071 604/95.01 |
| 2011/0184459 A1* | 7/2011 | Malkowski ........ A61B 17/29 606/206 |
| 2012/0010628 A1* | 1/2012 | Cooper ............ A61B 19/2203 606/130 |

* cited by examiner

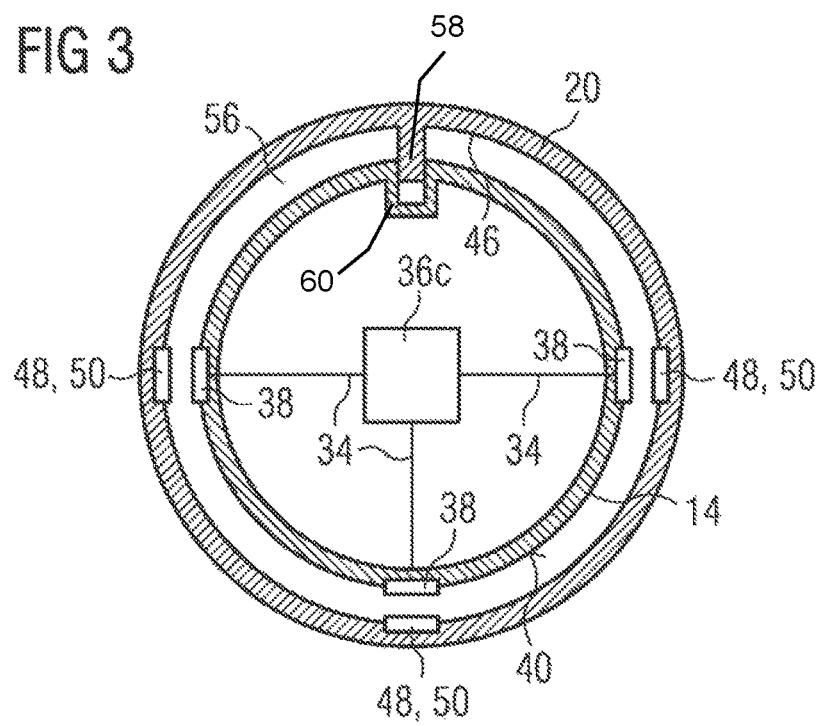
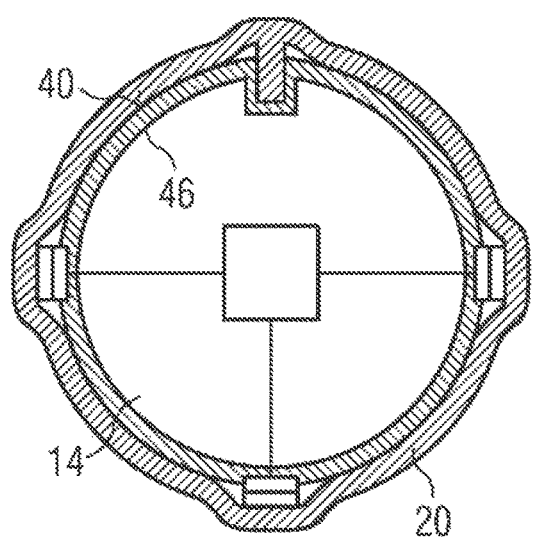

INSTRUMENT FOR A MANIPULATOR ARM OF AN ENDOSCOPIC ROBOT

CROSS REFERENCE TO RELATED APPLICATIONS

This application is the US National Stage of International Application No. PCT/EP2011/064781 filed Aug. 29, 2011 and claims the benefit thereof. The International Application claims the benefits of German application No. 10 2010 040 415.2 filed Sep. 8, 2010, both of the applications are incorporated by reference herein in their entirety.

FIELD OF THE INVENTION

The invention relates to an instrument for a manipulator arm of an endoscopic robot.

BACKGROUND OF THE INVENTION

In the field of clinical surgery minimally invasive surgical operations are growing in importance. Only a few years ago relatively large areas of the operative site were opened up even for minor surgical operations in order to enable the surgeon to navigate by means of natural landmarks. It may be observed that today a large number of these surgical operations are performed by means of laparoscopy and optical support in the form of endoscopy. In some areas of medicine, e.g. urology, gynecology or cardiology, robot-supported surgery as a development of traditional laparoscopy has been on the increase in the meantime and is in the process of establishing itself.

In the case of laparoscopy in the traditional sense, instruments which are used to carry out a medical measure inside a patient are introduced into the patient at least partially by means of a trocar and operated or controlled manually by a surgeon.

In the case of robot-supported surgery, a corresponding instrument is located on a manipulator arm of an endoscopic robot. Here too the instrument passes from outside the patient into the inside of the same. The robot arm always remains outside the patient. The robot or its control system therefore assumes the actual control of the instrument. The surgeon in turn controls only the robot with the aid of an operating interface. A known endoscopic robot is e.g. the "Da Vinci" system made by the company "Intuitive Surgical".

The known system constitutes a so-called tele-operated robot assistance system, in which a surgeon manually performs movement inputs on an operator console. The robot then transmits the scaled movements via appropriate kinematics to the instruments inside the body of the patient. Such systems play a decisive role in market development. There are numerous possible solutions to the design of the kinematics of the assistance system which have hitherto been characterized by an inconveniently large requirement for space.

Namely it is known, e.g. from the aforementioned "Da Vinci" system, not to provide the required mobility in the instrument itself but by means of the part of the endoscopic robot located outside the patient, namely the manipulator arm. The manipulator arm therefore constitutes the prime extracorporeal positioning unit for the instrument. The instrument itself is more or less rigid and also fixed rigidly to the manipulator arm. As a rule, the entry point through the trocar forms a pivotal point for the available movements. In any case, the actual treatment head of the instrument can be moved on the instrument, e.g. in the form of a pair of scissors or a gripper which can be operated. The instrument itself therefore only displays a single degree of freedom, e.g. opening or closing of the arms of the gripper.

The known "Da Vinci" system has up to four manipulator arms which can be moved individually. In order to realize the aforementioned degrees of freedom of the instrument movement, these are elaborately constructed and require a large volume of space in which to move.

In contrast, it is also possible to counteract this disadvantage using newer designs. For example, it is possible to propose improved instruments which themselves enable greater freedom of movement than the rigid instruments known hitherto.

The manipulator arms can then provide less scope for movement and as a result can be designed more simply and with a smaller requirement for space.

Intrinsically mobile instruments also make it possible to economize on manipulator arms as several instruments can be held on one arm which nevertheless can then be moved relative to each other on account of their intrinsic mobility. As a result of the fact that the instruments or endoscopes themselves have greater degrees of freedom of movement, the working area required by the endoscopic robot or its manipulator arm outside the body therefore remains limited. The principal part of the surgery movement is replaced by a greater degree of kinematic freedom within the operative site.

Depending on the distribution of the degrees of freedom across the manipulator arm and instrument, the combination of a mobile instrument with a corresponding manipulator arm results in an endoscopic robot with at least partial intracorporeal operation.

The challenge of the latter approaches now consists of realizing the multiplicity of instruments and degrees of freedom of movement in the case of a small instrument diameter. Namely, the instruments must as a rule be introduced into the patient by means of a trocar with an internal diameter of approx. 10 mm maximum or be moved through the trocar.

Another problem is that a business model can increasingly be found in relation to medical instruments in which the instruments are supplied as one-time-use instruments, so-called disposables. This results in a demand for instruments with a low cost position that can at the same time be sterilized with ease. All of the aforementioned challenges have hitherto met with realization problems.

In a mobile instrument it is conceivable to drive the axes of the instrument degrees of freedom principally by means of wire cable designs, wherein the wire cables are finally driven by the endoscopic robot. The aim of this approach is to remain as cost-effective as possible on the basis of a desired disposable design. For every degree of freedom in the instrument at least two wire cables must be fed through the instrument structure in order to be able to realize both directions of movement at a force or torque which can be dosed.

For an instrument with a scope of movement which is intended to cover five degrees of freedom and a mobile treatment head with one function, ten plus two wire cables must therefore be provided at the most unfavorable position, namely between the robot arm and the first joint. Both the latter then serve to provide end effector functionality, e.g. the actuation of a pair of scissors or a gripper. All the wire cables must be fed through the structure at least at the fastening end of the instrument. This is expensive.

Additional axes of motion can be brought about by moving the mounting bracket of the instrument on the robot arm itself. However, these do not constitute any real mobility of the instrument, in other words relative to the robot arm.

To be sure, such an instrument can be constructed, for example, with a diameter of 8 mm. However, no installation space of any kind is left, for example, to incorporate another electrical power cable into the instrument as would, for example, need to be supplied at the tip of the instrument for an HF blade as a treatment head.

On the other hand, the sterilizing capability of such a design, for example precisely in the area of a bend or a joint, must be called into question. Scalability to yet more degrees of freedom with the same or an even smaller diameter is in all probability not currently practicable in terms of technology.

Alternatively, the use of direct drives with sufficient power density or upstream gears for each individual joint is conceivable in corresponding instruments. However, a disposable design for such an instrument does not at least appear to be feasible on account of the anticipated costs. In addition, available direct drives, for example piezoelectric drives with appropriate performance data, have a space requirement which already takes up the majority of the diameter of an instrument. Additional energy and signaling lines which are to be fed past the direct drive are therefore difficult to accommodate in the interior of the instrument. The advantage of this approach, however, resides in the fact that with a constant diameter such a system design is scalable and both the structural and production complexity of the instrument is reduced.

SUMMARY OF THE INVENTION

The object of the present invention is to specify an improved instrument for a manipulator arm of an endoscopic robot.

The object is achieved by an instrument as claimed in the claims. The instrument contains a treatment head for carrying out a medical measure in a patient. In addition, the instrument comprises an instrument base which carries the treatment head, wherein the instrument base comprises a coupling element that can be fastened to the manipulator arm. The instrument has a sterilizable sleeve enclosing the instrument base at least. The sleeve has at least one opening which can be sealingly placed on the instrument base, the coupling element protruding from said opening.

As a rule the sleeve also has a second opening from which the actual instrument, in other words the treatment head of the instrument, protrudes. As a rule, the opening is designed in such a way that the sleeve can be pulled over the instrument thanks to the opening. The instrument base is, for example, oblong in design, wherein the coupling element is then located at one longitudinal end, with which the instrument is turned towards the manipulator arm. The treatment head, for example a pair of scissors, a gripper or an HF end effector, is then located at the other longitudinal end of the instrument base.

In other words, the proposal is therefore to cover most of an instrument of any complexity with a sterilizable—or naturally also sterile—sleeve. The insertion points, in other words openings of the sleeve, are sealed in relation to the instrument in the process. In this way, at least the instrument parts enclosed by the sleeve have a sterile seal with the surgical site. The sterilizing capability of the instrument or instrument base itself is therefore no longer of crucial importance and need not be taken into consideration in the design of the instrument.

In a preferred embodiment of the invention the sleeve has a shrinking property which at least in the area of the opening can be triggered by heating in order to bring about the sealing contact on the instrument base when fitting the sleeve. In other words, the sleeve therefore has heat-shrink properties to create a sterile barrier at least at the opening between the instrument base and the operative site. The sealing system after shrinking can also be used in the form of frictional contact properties for the mechanical fastening of the sleeve to the instrument base.

In a further preferred embodiment, the sleeve is a tube with an opening at both ends. The tube-shaped sleeve thus has two openings through which the treatment head and the coupling element protrude from the sleeve. Such a sleeve is suitable in particular for oblong, for example rod-shaped instrument bases. Both openings can be sealingly placed on the instrument base to create a sterile barrier. In particular such a tube can, for example, be designed as heat-shrinkable tubing along its entire length. By heating the tube after placing it over the instrument base, it forms a sterile seal over the entire surface and is consequently stable with a frictional connection on the instrument base, and is held securely on the same as a result.

In a preferred embodiment of the instrument, the instrument base has at least two arm segments connected by at least one joint. The sleeve then comprises fitting segments which are located in the region of the arm segments and are in contact with them there. In the region of the joints, on the other hand, the sleeve has joint segments which enable movement of the joints. For example, in the region of the joint segments the sleeve displays no shrinking properties or is even radially extended accordingly, for example in the form of ventilation bag segments not in contact with the instrument base. In particular, therefore, joints which as a rule are difficult to sterilize present no problems as they are sealed by the sterile sleeve and therefore do not have to be sterilized themselves.

In other words, in this embodiment a longitudinally structured tube with alternating flexible joint components or corresponding close-fitting longitudinal sections is therefore placed over the instrument or the instrument base. The elements of the tube lying over straight instrument parts have heat shrink properties, with the result that during pre-operative heating the instrument is sealed by the tube. The flexible joint elements of the tube do not contract or are designed in such a way that after the contraction of the tube free movement of the joint is still possible. The entire instrument and above all, for example, the rotary joints of the instrument are protected from contamination by the tube. The tube provides a sterile barrier for the entire instrument.

In a further embodiment the sleeve contains a cable which extends along the instrument base from the area of the coupling element in the direction of the treatment head. The cable can therefore extend over the entire length or only over part of the length of the sleeve. The formulation "in the area of the coupling element" should be understood in the sense that in the case of the instrument mounted on the robot, it is possible to connect the cable to a corresponding counterpiece of the endoscopic robot in its vicinity. In this connection, the cable may extend on both the outside as well as the inside of the sleeve. The cable may be used for any purpose, thus for example as an electric cable or a hollow transport cable for fluid or gas.

In other words, cables can therefore be integrated in the sleeve tube itself which, for example, are used to supply electrical power to instrument components; for example energy or signaling lines. For example, the realization of a three-strand communication bus in the sleeve for the control of individual components or drives in the instrument via a signaling line for functional control and two additional lines for the drive energy is conceivable.

A controller assigned to a drive inside an instrument analyzes the bus signal and controls the instrument axes assigned to it in accordance with the specifications. In principle, any kind of energy and signals can be transmitted to any point of the instrument structure in particular in the case of integration of the cables into a plastic material as a sleeve and the associated excellent insulation properties of the sleeve. For example, transmission of HF energy to the end effector in the form of the treatment head via an HF cable running through the sleeve is conceivable.

In a further preferred embodiment the instrument base and/or the treatment head has an electric element. The cable integrated into the sleeve is then an electric cable in contact with the electric element. The contact between the cable and the electric element of the instrument base takes place, for example, when the sleeve is in place via contiguous contact surfaces on the inside of the sleeve and on the outside of the instrument base. The electric element can be, for example, a drive, a probe or a lighting device. In other words, the contact between the sleeve tube and the instrument base is guaranteed by elements which are in contact between the tube and instrument structure.

It is possible to put the respective cable, which is part of the sleeve, in direct contact with the sleeve, i.e. to connect it to a corresponding connection of the robot. To this end, for example, connectors must be provided on the sleeve.

In a preferred embodiment of the invention, however, the cable in the region of the coupling element is supplied on a connection arranged on the instrument base, communicating with the cable, and which can be connected to the endoscopic robot.

In other words, the cable in the region of the coupling element is fed back from the sleeve to or into the instrument base or the coupling element. A corresponding connection is then provided there. A counterpiece to the connection is then found in the manipulator arm. In other words, the contact of the cable with the endoscopic robot is finally nevertheless brought about via the end of the instrument base or the coupling element facing the endoscopic robot. A corresponding end piece of the instrument base, for example made from metal, can be better provided with connections, for example in the form of plugs or sealed connection pipes, than the as a rule flexible plastic sleeve. In other words, the external energy and signal transmission of the instrument finally takes place via the instrument base. However, continuation along the instrument takes place via the sleeve.

In a further preferred embodiment the inside of the sleeve has a form fit element which engages in a counterpiece element on the instrument base in such a way that the position of the sleeve on the instrument base is fixed. As a rule, the inside of the sleeve fits closely to the instrument base for the most part. In other words, when putting the sleeve on the instrument base their relative assembly position in relation to each other is therefore fixed. Thus, for example, it is ensured that contacts on the inside of the sleeve fit closely to correspondingly positioned counter-contacts of the instrument base. It is also ensured that joint segments of the sleeve are positioned in the region of the joints of the instrument base.

For example, in the case of a rod-shaped instrument and a corresponding sleeve tube, the rotational position of the tube in a circumferential direction is ascertained as follows: a groove running in a longitudinal direction is found on the instrument base. A radial inward lug on the inside of the sleeve fitting into the groove is located on the inside of the sleeve. Both elements must be lined up when the tube is assembled. The correct longitudinal position of the tube on the instrument base can be easily ascertained and ensured as a result of both the coupling element and the treatment head having to protrude from the tube. A certain amount of scope for the final longitudinal positioning of the tube on the instrument can, for example, be achieved by manufacturing corresponding contacts on the inside of the sleeve and counter-contacts on the instrument base in a longitudinal direction of the instrument above a certain tolerance range.

In a further preferred embodiment the sleeve is a sterile, disposable sleeve which can be removed from the instrument base. Thus, a disposable design is also possible for elaborately structured instrument bases as the disposable design is transferred from the instrument itself to its sleeve. As a consequence, the disposable design is now also being adopted as a business model, for example for elaborate and expensive directly driven instruments. As the tube serves as a sterile barrier, the instrument or the instrument base itself is protected from contamination and can be reused.

A corresponding disposable design is also suitable, for example, for modular instrument systems in which each respective instrument is composed of individual parts from a construction kit. A construction kit contains various treatment heads which can be combined with various joint and arm segments to form various instruments. After completion of the medical measure the sleeve is removed from the instrument base and disposed of. The instrument is disassembled into its individual components. The individual components themselves can then be cleaned or, if need be, also sterilized with ease. For subsequent use, a new instrument is put together from individual components of the construction kit and is provided with a disposable sleeve.

A design according to the invention is therefore proposed which also permits the realization of an instrument in direct drive form. The problems of sterilizing capability, cost position and energy and signal transmission are solved in the process. As a result of the properties according to the inventive and the local shifting of some design complexity from the interior of the instrument to its external sleeve, there is no longer anything to prevent the further miniaturization of instruments.

BRIEF DESCRIPTION OF THE DRAWINGS

For a further description of the invention, reference is made to the exemplary embodiments of the drawings. They show, respectively in a schematic diagram.

DETAILED DESCRIPTION OF THE INVENTION

Figure 1:
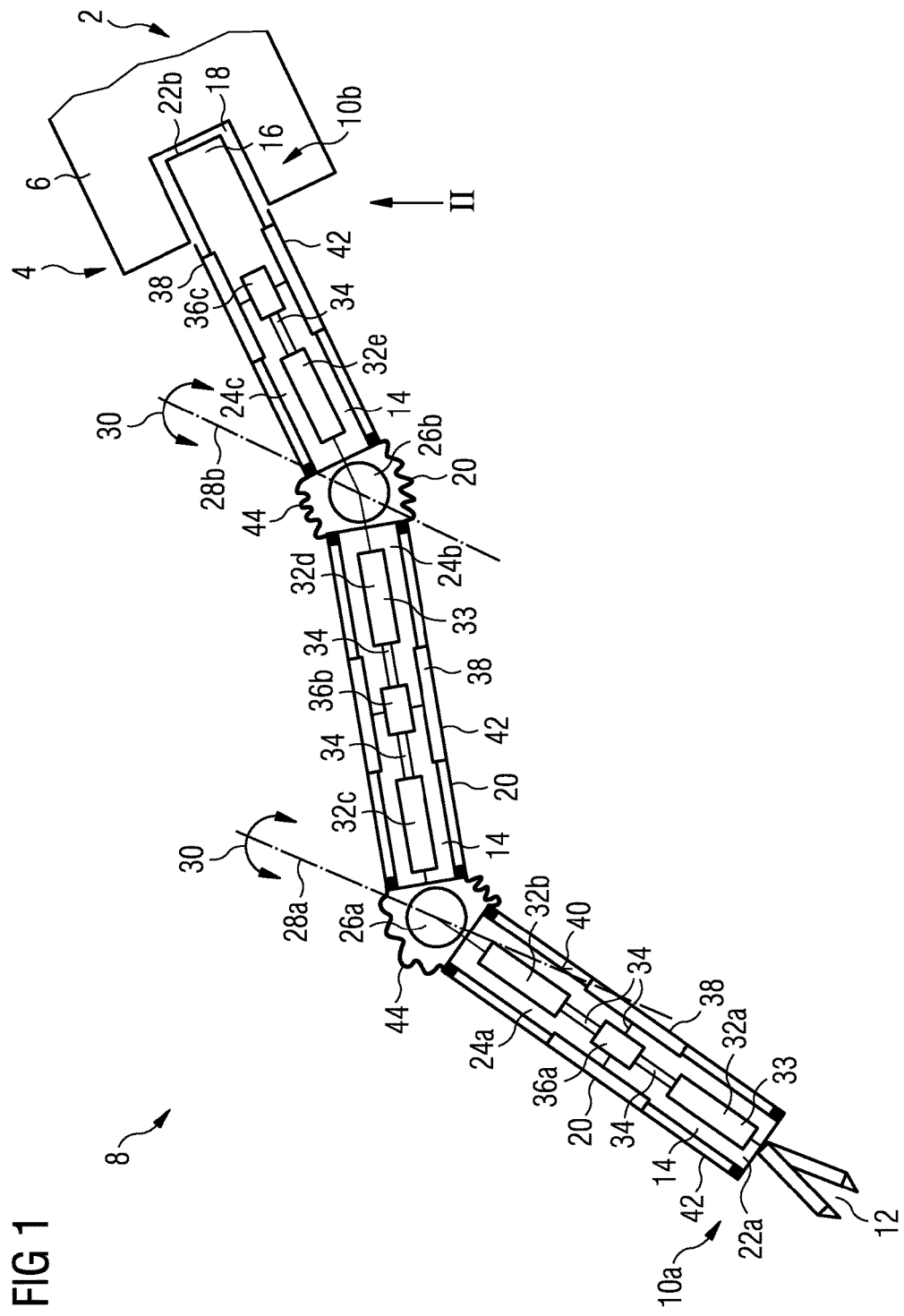
FIG. 1 an instrument according to the inventive.

FIG. 1 shows a section of an endoscopic robot 2, namely a front end 4 of its manipulator arm 6. An instrument 8 according to the invention is fastened to the manipulator arm 6. The instrument 8 is oblong and rod-shaped in design and at its front end 10a, in other words turned away from the manipulator arm 6, it has a treatment head 12, a pair of scissors in the example. The treatment head 12 is for carrying out a medical measure on a patient (not shown), in the present case for excising tissue.

The treatment head 12 is held on an instrument base 14 of the instrument 8, which extends from the treatment head 12 to the opposite end 10b of the instrument 8 or to the manipulator arm 6. At the end 10b the instrument base 14 has a coupling element 16 which is held fast in a receptacle 18 of the manipulator arm 6 but can be removed. The entire instrument 8 is therefore firmly connected to the manipulator arm 6. In FIG. 1 the end 10b of the instrument 8 or the receptacle in the manipulator arm 6 is only shown in diagrammatic form.

The instrument base 14 is enclosed by a sleeve 20 belonging to the instrument 8, which essentially extends from the end 10a to the end 10b. In the region of the ends 10a,b the sleeve 20 has two openings 22a,b, through which only the treatment head 12 and the coupling element 16 of the instrument 8 protrude from the sleeve 20. In other words, the sleeve 20 in FIG. 1 is therefore a tube with openings 22a,b at both ends. At both openings 22a and 22b the sleeve 20 is sealingly placed on the instrument base 14. The sleeve 20 itself is also sealed and sterile insofar as this forms a sterile barrier between the patient (not shown) and the instrument base 14.

The instrument base 14 is composed of three arm segments 24a-c, which are connected to each other via two joints 26a,b. With the aid of the joints 26a,b the arm segments 24a-c can be swiveled around respective axes of rotation 28a,b in the direction of the double arrows 30 relative to each other. Inside the instrument base 14 there are a number of direct drives 32a-e. The direct drive 32a activates the treatment head 12, the direct drives 32b,c, the joint 26a and the direct drives 32d,e the joint 26b. Each of the direct drives 32a-e is connected via a control cable 34 to one of three control units 36a-c in the respective arm segment 24a-c. The control units 36a-c are in turn connected via additional control cables 34 to contacts 38 on the outer surface 40 of the instrument base 14.

The direct drives 32a-e form electric elements 33 of the instrument 8 which must be supplied with a supply voltage and control signals.

The instrument 8 therefore constitutes a mobile double-jointed arm. The sleeve 20 therefore has three fitting segments 42 which are in contact with the external surface 40 in the region of the respective arm segments 24a-cc. In the region of both joints 26a,b, on the other hand, the sleeve has two joint segments 44 which permit the movement of the joints 26a,b or of the instrument 8 at this point.

Figure 2:
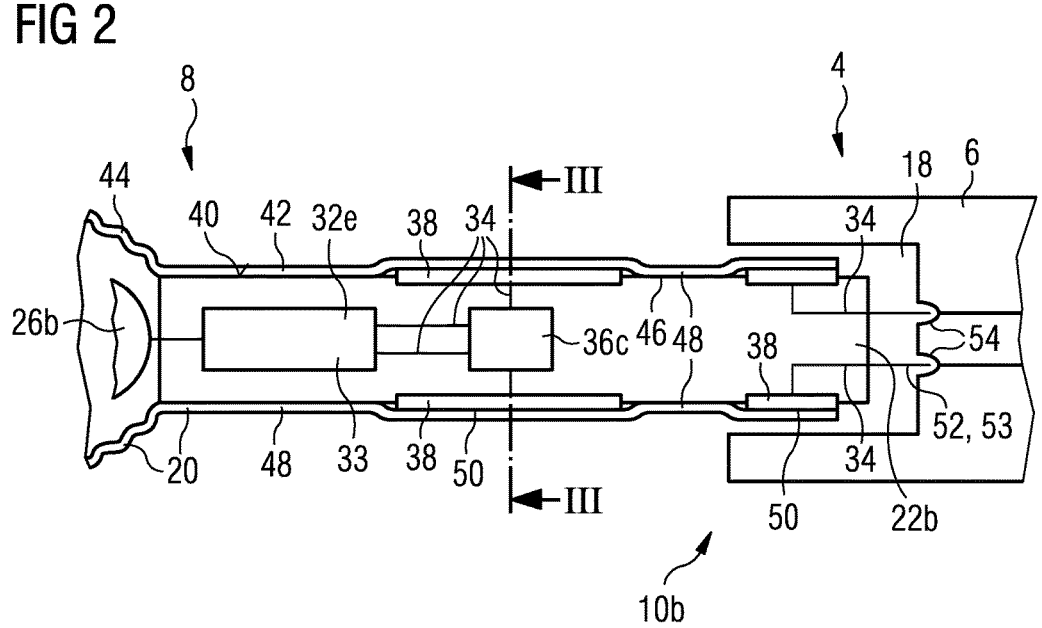
FIG. 2 in detail II from FIG. 1 the end of the instrument base with a coupling element, FIG. 3 a cross-section of the instrument from FIG. 2 along the line III-III after assembly, but before heating of the sleeve tube and FIG. 4 the situation in FIG. 3 after heating of the sleeve tube.

FIG. 2 shows the end 10b of the instrument 8 and its receptacle in the end 4 of the manipulator arm 6 as detail II from FIG. 1. The power supply of the instrument 8 or the direct drives 32a-e is also shown, cf. FIG. 1 again in this regard as well. To this end, the sleeve 20 has three cables 48 on its inside 46, which in this example are designed as electric cables. In FIG. 2 two of the cables 48 are visible. These are connected to contact surfaces 50, which are likewise located on the inside 46 of the sleeve 20. The contact surfaces 50 are geometrically arranged on the sleeve 20 in such a way that in the assembled state of the sleeve 20 on the instrument base 14 shown in FIG. 1 and FIG. 2 they are lined up with the contacts 38 of the instrument base 14. The elements 33 are therefore in electrical contact with the cables 48.

The electric cables 48 extend along the length of the instrument base 14 from the rearmost contact surface 38 at the end 10b of the instrument 8 to the foremost contact surface 38 on the arm segment 24a and thus connect all the contact surfaces 38 or the correspondingly connected control units 36a-c in the manner of a bus system. Each of the rearmost contacts 38 at the ends 10b of the instrument 8 visible in FIG. 2 are supplied via additional control cables 34 on contact studs 52. These protrude from the rear end face of the instrument base 14 at the end 10b. They are inserted into corresponding contact springs 54 of the manipulator arm 6 or of the receptacle 18 when the instrument 8 is used in the manipulator arm 6. Thus a simple electrical contacting of the instrument 8 or of the cables 48 of the sleeve 20 is achieved without having to separately contact the sleeve 20 directly via external contacts. The contact studs 52 in turn form connections 53 for the instrument 8.

FIG. 3 shows a section along the line in FIG. 2 through the instrument 8. However, FIG. 3 shows a different situation before the final assembly of the sleeve 20 on the instrument base 14. Here the sleeve 20 or the sleeve tube has an even larger internal diameter than the external diameter of the instrument base 14. Thus, radial clearance 56 is retained between both elements. This permits the sleeve 20 to be pulled in a longitudinal direction over the instrument base 14. In order to ensure that—seen from a radial direction with respect to a central longitudinal axis of the instrument 8—each of the contact surfaces 50 of the cables 48 are also facing the corresponding contacts 38 on the instrument base 14, an aid to orientation is given: a radial inward projection is provided on the sleeve 20 as a form fit element 58 which fits positively as a counterpiece element 60 to a groove in the instrument base 14. During assembly the sleeve 20 must be turned in a circumferential direction to the instrument base 14 in such a way that the form fit element 58 is enclosed in the counterpiece element 60. In this way at least the turning position between the sleeve 20 and the instrument base 14 is fixed. The correct axial position is produced, as can be seen in FIG. 1, by the sleeve 20 and the instrument base 14 having to fit flush with each other at the front end 22a of the instrument 8. Incorrect assembly of the sleeve 20 is thus avoided.

In addition, in FIG. 3 all three electrical connections of the control unit 36c, are identified representing all the control units 36a-c. The three connections are a positive and a negative power supply and an electric signal control cable in the manner of a bus.

The sleeve 20 has shrinking properties. For final assembly on the instrument base 14 this is therefore heated, as a result of which it contracts. The diameter of the sleeve 20 is reduced. In this way the respective contact surfaces 50 come into contact with the contacts 38 and form an electrical contact. In addition, the sleeve 20 continues to contract until it forms a tight seal on the instrument base 14. In other words, the outer surface 40 and the inside 46 are in contact, as a result of which the sleeve 20 is held tight on the instrument base 14 by means of friction. This applies to the area of the fitting segments 42. In the area of the joint segments 44, on the other hand, the sleeve 20 does not contract. In this way scope for movement is retained for movement of the joints 26a,b.

The invention claimed is:

1. An endoscopic robot, comprising:
   a manipulator arm; and an instrument fastened to the manipulator arm, wherein the instrument includes:
- a treatment head for carrying out a medical measure in a patient;
- an instrument base for carrying the treatment head; and
- a sterilizable sleeve enclosing the instrument base and having an opening constructed to be sealingly placed on the instrument base, wherein the instrument base includes a coupling element at one end, wherein the coupling element protrudes from the opening of the sterilizable sleeve, wherein the coupling element is constructed to be fastened to the manipulator arm, wherein the sterilizable sleeve is formed of a material having a shrinking property in an area of the opening, the shrinking property being triggered by heating for sealing contact on the instrument base, wherein the sterilizable sleeve having the shrinking property contains a cable extending from an area of the coupling element along the instrument base in a direction of the treatment head, and wherein the cable is disposed within the material of the sterilizable sleeve itself having the shrinking property.

2. The endoscopic robot as claimed in claim 1, wherein the sterilizable sleeve is a tube having openings at both ends.

3. The endoscopic robot as claimed in claim 1, wherein the instrument base includes arm segments connected by joints, and wherein the sterilizable sleeve includes fitting segments in an area of the arm segments closely fitting the area and includes joint segments in an area of the joints for enabling movement.

4. The endoscopic robot as claimed in claim 1, wherein at least one of the instrument base or the treatment head includes an electric element, and wherein the cable is an electric cable in contact with the electric element.

5. The endoscopic robot as claimed in claim 1, wherein the cable in an area of the coupling element is provided on a connection that is arranged on the instrument base, and wherein the connection is connected to an endoscopic robot and communicates with the cable.

6. The endoscopic robot as claimed in claim 1, wherein the sterilizable sleeve includes a form fit element disposed on an inner side of the sterilizable sleeve and engaging in a counterpiece element on the instrument base for fixing a position of the sterilizable sleeve on the instrument base.

7. The endoscopic robot as claimed in claim 1, wherein the sterilizable sleeve is a sterile disposable sleeve constructed to be removed from the instrument base.

* * * * *